United States Patent [19]
Kellerby

[11] Patent Number: 5,472,955
[45] Date of Patent: Dec. 5, 1995

[54] INSECTICIDE MIXTURE FOR EAR TAGS

[75] Inventor: Joe D. Kellerby, Cody, Wyo.

[73] Assignee: Y-Tex Corporation, Cody, Wyo.

[21] Appl. No.: 255,321

[22] Filed: Jun. 7, 1994

[51] Int. Cl.$^6$ .................................................. A01N 57/00
[52] U.S. Cl. ............................................. 514/86; 514/89
[58] Field of Search ........................................ 514/86, 89

[56] References Cited

U.S. PATENT DOCUMENTS

| | | | |
|---|---|---|---|
| 350,112 | 10/1886 | Burrows | 40/301 |
| 2,219,569 | 10/1940 | Vanderhoof | 119/96 |
| 3,731,414 | 5/1973 | Murphy et al. | 40/301 |
| 4,021,952 | 5/1977 | Brierley | 40/301 |
| 4,209,924 | 7/1980 | Fearing | 40/301 |
| 4,265,876 | 5/1981 | Feakins | 40/300 |
| 4,325,969 | 4/1982 | Brown | 424/304 |
| 4,581,834 | 4/1986 | Zatkos et al. | 48/301 |

FOREIGN PATENT DOCUMENTS 2041833  9/1980  United Kingdom .

OTHER PUBLICATIONS

Byford, R. L. et al., "Organophosphorus Insecticides for the Control of Pyrethroid–Resistant Horn Files (Diptera: Muscidae)," *J. Econ. Entomol.* 81:1562–1566 (1988).

Byford, R. L. et al., "Insecticide Mixtures as an Approach to the Management of Pyrethroid–Resistant Horn Flies (Diptera: Muscidae)," *J. Econ. Entomol.* 80:111–116 (1987).

Byford, R. L. et al., "Redistribution of Behaviorally Resistant Horn Flies (Diptera: Muscidae) on Cattle Treated with Pyrethroid–Impregnated Ear Tags," *Environ. Entomol.* 16:467–470 (1987a).

Byford, R. L. et al., "A Novel Resistance Management Strategy for Horn Flies (Diptera: Muscidae)," *J. Econ. Entomol.* 80:291–296 (1987b).

Byford, R. L. et al., "Insecticide Mixtures as an Approach to the Management of Pyrethroid–Resistant Horn Flies (Diptera: Muscidae)," *J. Econ. Entomol.* 80:111–116 (1987c).

Byford, R. L. et al., "Spectrum of Insecticide Cross–Resistance in Pyrethroid–Resistant Populations of *Haematobia Irritans* (Diptera: Muscidae)," *J. Econ. Entomol.* 78:768–778 (1985).

Cocke, J. Jr. et al, "Changes in Horn Fly Response to Diazinon and Fenvalerate Following Season Long Exposure to Various Pyrethroid and Organophosphate Ear Tags on Range Cattle in Texas," *Southwest Entomol.* 15:265–271 (1990).

Gordon, F. C. et al., "Efficiency of Japanese Beetle (Coleoptera: Scarabaeidae) Traps in Reducing Defoliation of Plants in the Urban Landscape and Effect on Larval Density in Turf," *J. Econ. Entomol.* 78:774–778 (1985).

Kunz, S. D. et al., "The Pyrethroid Resistance Problem in the Horn Fly," *J. Agric. Entomol.* 2:358–363 (1985).

Lockwood, J. A. et al., "Behavioral Resistance to the Pyrethroids in the Horn Fly, *Haematobia Irritans* (Diptera: Muscidae)," *Environ. Entomol.* 14:873–880 (1985).

Quisenberry, S. S. et al., "Pyrethroid Resistance in the Horn Fly, *Haematobia Irritans* (L.) (Diptera: Muscidae)," *J. Econ. Entomol.* 77:1095–1096 (1984).

Schmidt, C. D. et al., "Horn Fly: Modified Laboratory Rearing Methods," *Southwest Entomol.* 1:49–51 (1976).

Sheppard, D. C. et al., "Pyrethroid Resistance in Horn Flies: The Problem, Causes, and Possible Solutions," *J. Agric. Entomol.* 2:317–324 (1985).

Sparks, T. C. et al., "Insecticide Resistance in the Horn Fly, *Haematobia Irritans,*" *J. Agric. Entomol.* 2:217–233 (1985).

Worthing et al., The Pesticides Manual, 9th Ed. (1991) pp. 166, 167, 243 & 244.

Primary Examiner—Allen J. Robinson
Attorney, Agent, or Firm—Harness, Dickey & Pierce

[57] ABSTRACT

The present invention provides a composition effective in controlling animal ectoparasites, in particular, horn flies. The composition comprises diazinon and chlorpyrifos and has a synergistic effect as an insecticide. The composition of the present invention is particularly effective in controlling pyrethroid-resistant horn flies.

5 Claims, No Drawings

INSECTICIDE MIXTURE FOR EAR TAGS

FIELD OF THE INVENTION

The invention relates to compositions, methods and devices containing or employing a mixture of diazinon and chlorpyrifos which together provide a synergistic effect as an insecticide. The present invention is particularly useful as an insecticide either applied topically or in a sustained release delivery system, such as a polymer matrix for horn fly control.

BACKGROUND OF THE INVENTION

Recently, resistance to the active ingredients used in insecticide-impregnated ear tags has become a primary problem in the control of horn flies, *Haematobia irritans* (L.), throughout the Americas and in many other regions of the world. Kunz, S. D. et al., *J. Agric. Entomol.* 2:358–363 (1985). Many horn fly populations have been shown to be physiologically resistant (10- to 85-fold) to a variety of synthetic pyrethroid insecticides including permethrin, fenvalerate, flucythrinate, cyfluthrin, cypermethrin, and deltamethrin. Studies have also demonstrated the presence of a broad spectrum of cross-resistance to virtually all commercially available pyrethroids as well as to the organochlorine insecticides, DDT and methoxychlor. Byford, R. L. et al., *J. Econ. Entomol.* 78:768–778 (1985).

This resistance is due to both direct exposure of the horn fly population to specific pyrethroids and to a high level of cross-resistance to insecticides within this class. Byford, R. L. et al., *J. Econ. Entomol.* 78:768–778 (1985). In particular, the cross-resistance spectrum and results of studies using selected insecticide synergists indicate that pyrethroid-resistance in the horn fly is the result of several mechanisms, including an active site insensitivity similar to knockdown resistance (kdr) and enhanced detoxification. Byford, R. L. et al., *J. Econ. Entomol.* 78:768–778 (1985) and Sparks, T. C. et al., *J. Agric. Entomol.* 2:217–233 (1985). In addition, a modified behavior also appears to play a role in the ability of the horn fly to survive in the presence of pyrethroid-impregnated ear tags. Quisenberry, S. S. et al., *J. Econ. Entomol.* 77:1095–1096 (1984), Lockwood, J. A. et al., *Environ. Entomol.* 14:873–880 (1985) and Byford, R. L. et al., *Environ. Entomol.* 16:467–470 (1987a).

A variety of strategies have been proposed to counter resistance in the horn fly including rotation of insecticide classes, use of synergist-insecticide mixtures, regional application of insecticide classes in a "mosaic" pattern, and modification of the delivery systems. Sheppard, D. C. et al., *J. Agric. Entomol.* 2:317–324 (1985), Sparks, T. C. et al., *J. Agric. Entomol.* 2:217–233 (1985), Byford, R. L. et al., *J. Econ. Entomol.* 80:291–296 (1987b) and Byford, R. L. et al., *J. Econ. Entomol.* 80:111–116 (1987c). It has been shown that the use of other insecticides or synergists (or both) with a pyrethroid often increases the efficacy of the pyrethroid but usually does not eliminate the resistance problem. Typically, some level of resistance to the insecticide combination remains. Byford, R. L. et al., *J. Econ. Entomol.* 80:111–116. (1987c). Thus, alternative approaches must be found which provide long-lasting horn fly control without elevating resistance to pyrethroid insecticides.

It is therefore desirable to develop a sustained-release insecticide and insecticide device such as an impregnated ear tag, that is effective against pyrethroid-resistant horn flies and other ectoparasites of livestock such as ticks, lice, stable flies, face flies and house flies. It is also desirable to provide a sustained-release insecticide and insecticide device that has a long-term, high degree of efficacy against pyrethroid-resistant horn flies and other ectoparasites of livestock without elevating pyrethoid resistance.

SUMMARY OF THE INVENTION

The present invention comprises compositions, methods and devices effective as insecticides. The claimed inventions provide compositions, methods and devices (e.g., ear tags) which do not contain pyrethroids but are effective in controlling ectoparasites such as horn flies. The claimed compositions comprise two organophosphate insecticides, chlorpyrifos and diazinon, which when combined, have a heretofore unappreciated and unexpected synergistic effect as an insecticide. The present invention therefore preferably comprises a composition employing a mixture of chlorpyrifos and diazinon effective as an insecticide.

In a preferred embodiment of the present invention, the ratio of diazinon to chlorpyrifos is about 3 to 1 by weight, (i.e., about 75% diazinon and 25% chlorpyrifos). However, it will be appreciated that a ratio of diazinon to chlorpyrifos from about 1:10 to about 10:1, and other combinations of the compounds which yield the desired result, are also contemplated by the present invention. The appropriate dosage will also vary depending on the delivery system employed, the environment of use, as well as the desired result. The typical impregnation level for impregnated ear tags employed for the control of horn flies is in the range of from about 8% to about 40%. A preferred range for this invention is from about 20% to about 40%. It will be appreciated that other effective impregnation levels are also contemplated by the present invention.

Delivery of the composition to the animal may be by various slow-release systems including impregnated ear tags, collars, membrane devices, suspended rope wicks, miniature pumps and porous materials. It will be appreciated that other modes of sustained-release delivery known in the art are also contemplated by the present invention.

DETAILED DESCRIPTION OF THE PREFERRED EMBODIMENTS

Chlorpyrifos, $C_9H_{11}Cl_3NO_3PS$, is well known in the art having been disclosed in French Patent No. 1,360,901 corresponding to U.S. Pat. No. 3,244,586 and is available under the tradenames DOWCO 179, ENT 27311, Dursban, Lorsban, Pyrinex and others. Diazinon, $C_{12}H_{21}N_2O_3PS$, is likewise well known in the art having been disclosed in U.S. Pat. No. 2,754,243 and is available under the tradenames Basudin, Diazol, Garden Tox, Neocidol, Sarolex, Spectracide and others.

Both chlorpyrifos and diazinon have been evaluated individually in laboratory bioassays and in field tests of formulated products as potential insecticides to horn flies. As reported in Byford, R. L. et al., *J. Econom. Entomol* 81:1562–1566 (1988), in laboratory topical bioassays, diazinon was slightly more toxic than the pyrethroid permethrin to a pyrethroid-susceptible strain of horn flies and exhibited a similar level of toxicity to pyrethroid-resistant horn flies. Consequently, in field tests of formulated ear tags, diazinon has produced acceptable control of pyrethroid-resistant horn fly populations for 3 to 5 months. Chlorpyrifos on the other hand, is much less toxic to either susceptible or pyrethroid-resistant horn flies than diazinon and it has not provided acceptable control of horn flies in field tests of formulated chlorpyrifos tags, even with ear tags containing much higher concentrations of chlorpyrifos than what is typical for diazinon formulations.

Chlorpyrifos has also been studied in mixtures with pyrethroids. As reported in Byford, R. L. et al., *J. Econom. Entomol.* 80:111–116 (1987), the addition of chlorpyrifos to pyrethroids increased their toxicity but did not significantly change resistance ratios compared with pyrethroids alone. Field evaluations of some formulated tags revealed that several mixtures did not control resistant horn fly populations below economically damaging levels for adequate time periods.

Although both chlorpyrifos and diazinon have been individually studied as potential insecticides to horn flies, when the compounds are combined it has been found that they have a heretofore unappreciated and unexpected synergistic effect, as is discussed in detail below.

Experimentation was performed to determine contact toxicity to horn flies using treated filter paper in petri dishes. The experimental test procedures employed were the same as those described in Sheppard et al., *J. Agric. Entomol.* 2:317–324 (1985), herein incorporated by reference. In particular, resistant and susceptible horn flies were collected from horn fly colonies maintained by the New Mexico State University Department of Entomology, Plant Pathology and Weed Science in Las Cruces, N. Mex., as adults and maintained according to the methods of Schmidt, C. D. et al., *Southwest Entomol.* 1:49–51 (1976) and Byford, R. L. et al., *J. Econ. Entomol.* 78:768–778 (1985). Contact bioassays were performed on adult horn flies (3–5 days old) as described in Sheppard, et al., *J. Agric. Entomol.* 2:317–324 (1985). Horn flies were treated in groups of 20 to 30. Tests were replicated three to five times. Mortality was determined 2 hours after treatment and analyzed by probit analysis (MicroProbit 3.0 for the IBM PC, T. C. Sparks and A. Sparks). Finney, D. J. Probit. Analysis 3rd Ed. Cambridge University, Cambridge (1971). For each insecticide, resistance ratios were calculated by diving the $LC_{50}$ determined for the resistant strain with the $LC_{50}$ of the susceptible strain. Lack of overlap between the fiducial limits of the two dose mortality regression lines was used as the criterion for statistical significance.

As detailed above, the contact toxicity of diazinon, a diazinon and piperonyl butoxide (PBO) solution, and a diazinon and epoxidized soybean oil (ESO) solution to horn flies was studied and the results are shown in Table I along with corresponding synergism indicator ratios. The $LC_{50}$ and $IC_{90}$ data depicted in Table 1 and described below were measured in $\mu g/cm^2$ of treated filter paper using the test method described by Sheppard, D. C. et al., *J. Agric. Entomol.* 2:317–324 (1985). Against a pyrethroid-resistant horn fly colony in 1991, diazinon alone exhibited a $LC_{50}$ of 0.47, diazinon plus PBO exhibited a $LC_{50}$ of 0.57 and diazinon plus ESO exhibited a $LC_{50}$ of 0.44. Against pyrethroid-resistant horn flies, diazinon had a $LC_{50}$ of 0.60, the diazinon and PBO solution had a $LC_{50}$ of 0.57 and the diazinon and ESO solution had a $LC_{50}$ of 0.53.

A similar study was performed in 1992 wherein chlorpyrifos alone and in combination with diazinon was tested. As shown in Table 1, against pyrethroid-susceptible horn flies, diazinon alone had a $LC_{50}$ of 0.70 and a $LC_{90}$ of 0.99. Chlorpyrifos alone had a $LC_{50}$ of 1.43 and a $LC_{90}$ of 6.33. A diazinon and chlorpyrifos mixture in a ratio of 3:1, by weight, had a $LC_{50}$ of 0.54 and a $LC_{90}$ of 0.91. Against pyrethroid-resistant horn flies, diazinon alone had a $LC_{50}$ of 0.70 and $LC_{90}$ of 0.99. Chlorpyrifos alone had a $LC_{50}$ of 1.19 and a $LC_{90}$ of 5.13. Diazinon and chlorpyrifos combined in a ratio of 3:1 had a $LC_{50}$ of 0.37 and a $LC_{90}$ of 0.60. To assist in determining the synergistic effects of the active compounds of the mixture, two ratios, diazinon synergism ratio and chlorpyrifos synergism ratio were defined. The diazinon synergism ratio ($DSR_{50}$), computed for pyrethroid-resistant horn flies, was defined as the diazinon $LC_{50}$ divided by the $LC_{50}$ of the diazinon:chlorpyrifos mixture. The $DSR_{50}$ was thus computed to be 1.9 for the diazinon:chlorpyrifos mixture combined in a ratio of 3:1. The chlorpyrifos synergism ratio ($CSR_{50}$), defined similarly and computed as the chlorpyrifos $LC_{50}$ divided by the $LC_{50}$ of the mixture for resistant horn flies, was 3.2. The resistance ratio ($RR_{50}$), calculated as the resistant $LC_{50}$ divided by the susceptible $LC_{50}$, was 1.00 for diazinon, 0.83 for chlorpyrifos and 0.68 for the diazinon:chlorpyrifos mixture combined in a ratio of 3:1. Similar synergistic activity was observed in laboratory tests against stable flies (*Stomoxys calcitrans*) and house flies (*Musca domestica*). The results are shown in Table 2.

Ear tags which are attached to the ears of animals for identification purposes are also well known. Such tags can be made of a plastic material or of a suitable metal and can take the form of a single element or band, one end of which is capable of piercing an animal's ear and making a firm connection with the other end of the element or band; alternatively they can take the form of a two-component tag comprising a male component having a pointed pin which is adapted to be forced through an animal ear and a female component which can be urged over the pointed end of the pin to retain the male component in position on the ear. The means of identification, i.e., the tag itself, can be attached to or integrally formed with the single element or band or either or both components of the two-component tag. U.S. Pat. No. 1,337,882 describes a two-component tag and also illustrates one type of applicator which is a pair of modified pliers for attaching such tags to animal ears. A highly preferred tag is disclosed in U.S. Pat. No. 4,581,834 to Zatkos, Kellerby and Knapp, herein incorporated by reference, and this patent also illustrates a preferred type of tag applicator which provides a rectilinear fastening motion.

Accordingly, the present invention also provides (without limitation) an ear-tag for attachment to an ear of an animal wherein at least part of the tag is made from a material comprising a solid organic polymeric or copolymeric substance forming a cross-linked matrix having a molecular weight range of about 60,000 to about 800,000, with an average preferably above 100,000, and an effective amount of a pesticidally-active mixture of diazinon and chlorpyrifos.

The tag may include the material or may be formed from the said material. Alternatively, only part of the tag, for example a single component of a two-component tag, may be made of the said material. In yet another embodiment, the tag is formed entirely of the said material.

The polymeric substance or matrix may be thermosetting or thermoplastic, although the latter is more readily employed in the manufacture of an ear-tag of the invention. Examples of suitable substances are polyolefins (for example polyethylene, polypropylene and copolymers of ethylene and propylene): polyacrylates (for example polymers and copolymers of methyl acrylate, ethyl acrylate, methyl methacrylate and ethyl methacrylate); polymers of vinyl compounds (for example polystyrene and polymerized divinylbenzene); polyvinyl halides (for example polyvinyl chloride); polyvinyl acetals (for example polyvinyl butyryl); polyvinylidene compounds (for example polyvinylidene chloride); synthetic and natural elastomers (for example rubber obtained from hevea brasiliensis, cis-1,4-polyisoprene, acrylonitrile-butadiene copolymers (NBR), polybutadiene styrene-butadiene copolymers (SBR)) and; urea-formaldehyde and melamine-formaldehyde resins; epoxy resins (for example polymers of polyglycidyl ethers of polyhydric phenols); cellulose plastics (for example cellulose acetate, cellulose butyrate and cellulose nitrate); and polyurethanes. It will be appreciated by the skilled artisan that the choice of the polymeric matrix system will depend both on the particular pesticide mixture with which it is to be formulated and the conditions under which the final formulation will be employed. To be most effective, it is preferably insoluble in water and presents a hydrophobic surface, thus resisting the absorption of moisture on its surface which could dilute the active ingredients.

Preferably, the polymeric substance or matrix may include a polymer or a copolymer of a vinyl compound, for example polyvinyl halides (for instance polyvinyl chloride and polyvinyl fluoride); polyacrylate and polymethacrylate esters (for instance polymethyl acrylate and polymethyl acrylate and polymethyl methacrylate); and polymers of vinyl benzenes (for instance, polystyrene and polymer polymerized vinyl toluene). Because it possesses desirable physical properties with desirable release rate characteristics for the pesticide, one of the preferred macromolecular substances is a polymer of vinyl chloride.

It is generally necessary to include a plasticizer in the polymeric substance or matrix in order to enable satisfactory ear-tags to be formed from it. Examples of plasticizers are phthalates (i.e., dioctyl phthalate, diphenyl phthalate, dicyclohexyl phthalate, dimethyl phthalate and dihexyl phthalate); sebacates (i.e., dipentyl sebacate, n-butyl benzyl sebacate and dibenzyl sebacate); adipates (i.e., isobutyl adipate, dioctyl adipate and dinonyl adipate); citrates (i.e., acetyltributyl citrate and acetyl triethyl citrate), and trimellitates. Other compatible plasticizers are, for example, hydrogenated polyphenols; alkylated aromatic hydrocarbons; polyester plasticizers, for example polyesters of polyols, such as hexanediol, polycarboxylic acids, such as sebacic or adipic acid, having molecular weights of about 2000, and epoxide plasticizers such as epoxidized soybean oil, epoxidized linseed oil and epoxidized tall oils (such as octyl epoxy tallate).

Other materials such as dyes, pigments, lubricants, fillers, anti-oxidants and ultraviolet stabilizers may be included in the formulation. For example, it has been found that the stability of the formulation is extended if amounts of 0.10% to about 0.25% by weight, of each one or more suitable chemical stabilizers are included. For example, certain hydroxycinnamates (such as IRGANOX® 1076, Octadecyl 3,5 -di-tert-butyl-4-hydroxyhydrocinnamate) and benzotriazoles (such as TINUVIN® P, 2 -(2'-Hydroxy-5'-methylphenyl)benzotriazole) are effective as stabilizers against heat and ultraviolet light degradation.

The ear-tag may be manufactured by any convenient means, but preferably by injection-molding techniques. Other techniques may include casting, laminating, and die-cutting.

The concentration of the pesticide mixture in the portion of the ear-tag that incorporates said pesticide may vary between 10% and 50% by weight. The preferred concentration range is from 30% to 45% by weight, and the optimum concentration is approximately 40% by weight of the ear-tag. Concentrations falling in these ranges have produced good control of cattle ectoparasites such as horn flies resistant to pyrethroids, face flies, stable flies, biting lice, sucking lice, ear ticks, and certain species of body ticks.

TABLE 1

Diazinon/Chlorpyrifos Synergism Data by Contact Toxicity To Horn Flies (Haematobia irritans) On Treated Filter Paper

| Year Tested | Insecticide | Pyrethroid-Susceptible Horn Flies | | Pyrethroid-Resistant Horn Flies | | Indicator Ratios | | |
|---|---|---|---|---|---|---|---|---|
| | | $LC_{50}$ | $LC_{90}$ | $LC_{50}$ | $LC_{90}$ | $RR_{50}^3$ | $DSR_{50}^4$ | $CSR_{50}^5$ |
| 1991 | Diazinon | 0.47 | 0.82 | 0.60 | 1.05 | 1.28 | — | — |
| | Diazinon + PBO[1] | 0.57 | 0.94 | 0.57 | 1.05 | 1.00 | 1.0 | — |
| | Diaz. + ESO (1/1)[1] | 0.44 | 0.97 | 0.53 | 0.81 | 1.20 | 1.1 | — |
| 1992 | Chlorpyrifos | 1.43 | 6.33 | 1.19 | 5.13 | 0.83 | — | — |
| | Chlor. + PBO (1/1)[1] | 5.00 | 10.43 | 2.76 | 10.34 | 0.55 | — | 0.4 |
| | Diazinon | 0.70 | 0.99 | 0.70 | 0.99 | 1.00 | — | — |
| | Diaz. + PBO (1/1)[1] | 1.01 | 1.42 | 0.76 | 1.03 | 0.75 | 0.9 | — |
| | Diaz. + Chlor.(3/1)[2] | 0.54 | 0.91 | 0.37 | 0.60 | 0.68 | 1.9 | 3.2 |

[1](1/1) mixtures are amounts of 50% diazinon or chlorpyrifos + 50% piperonyl butoxide (PBO) or epoxidized soy oil (ESO).
[2](3/1) mixtures are amounts of 75% diazinon + 25% chlorpyrifos.
[3]$RR_{50}$ = Resistance Ratio = Resistant $LC_{50}$ ÷ Susceptible $LC_{50}$.
[4]$DSR_{50}$ = Diazinon Synergism Ratio = diazinon $LC_{50}$ ÷ mixture LC (as if 100% diazinon) for pyrethroid-resistant horn flies.
[5]$CSR_{50}$ = Chlorpyrifos Synergism Ratio = chlorpyrifos $LC_{50}$ ÷ mixture $LC_{50}$ (as if 100% chlorpyrifos) for pyrethroid-resistant horn flies.

The preferred concentration of 40% diazinon:chlorpyrifos mixture (30:10) in an ear tag has also been found in field tests to be highly effective against biting and sucking lice of cattle. In fact, 1992–1993 winter tests at the University of Wyoming showed that one ear tag containing the 40% mixture was much more active than two ear tags per animal containing 21.4% diazinon as the only active ingredient, particularly against sucking lice species.

Thus, as can be appreciated by the results set forth above, the mixture of diazinon and chlorpyrifos has a synergistic effect on the contact toxicity of pyrethroid-susceptible and pyrethroid-resistant horn flies. It should also be appreciated that the composition of the present invention may also be used as an insecticide against other plant and animal insect pests.

TABLE 2

Diazinon and Chlorpyrifos Contact Toxicity and Mixture
Syergism Data Against Stable Flies (Stomoxys calcitrans)
and House Flies (Musca domestics) on Treated Filter Paper, 1992.

| Insecticide | Stable Fly | | | | House Fly | | | |
|---|---|---|---|---|---|---|---|---|
| | $LC_{50}$ | $LC_{90}$ | $DSR_{50}$ | $CSR_{50}$ | $LC_{50}$ | $LC_{90}$ | $DSR_{50}$ | $CSR_{50}$ |
| Diazinon | 3.31 | 4.64 | — | — | 15.98 | 71.73 | — | — |
| Chlorpyrifos | 4.77 | 16.83 | — | — | 25.46 | 264.31 | — | — |
| Diaz. + Chlor. (3/1) | 2.73 | 3.94 | 1.2 | 1.7 | 11.94 | 67.00 | 1.3 | 2.1 |

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

I claim:

1. An insecticidal composition comprising synergistic insecticidally effective amounts of a mixture of diazinon and chlorpyrifos, wherein the ratio of the diazinon to chlorpyrifos is about 5:1 to about 1:1.

2. The composition of claim 1, wherein the ratio of diazinon to chlorpyrifos is about 3:1 by weight.

3. A method for the control of ectoparasites of animals comprising the step of contacting the ectoparasites with synergistic insecticidally effective amounts of a composition comprising diazinon and chlorpyrifos, wherein the ratio of diazinon to chlorpyrifos is about 5:1 to about 1:1.

4. The method of claim 3, wherein the ratio of diazinon to chlorpyrifos is about 3:1 by weight.

5. The method of claim 3, wherein the ectoparasites are horn flies, *Haematobia irritans*, stable flies, *Stomoxys calcitrans*, and house flies, *Musca domestica*.

* * * * *